United States Patent [19]

Cohen et al.

[11] Patent Number: 5,494,682
[45] Date of Patent: *Feb. 27, 1996

[54] IONICALLY CROSS-LINKED POLYMERIC MICROCAPSULES

[75] Inventors: Smadar Cohen, Petach-Tickya, Israel; Carmen Bano, Valencia, Spain; Karyn B. Visscher, State College, Pa.; Marie Chow, Brookline, Mass.; Harry R. Allcock, State College, Pa.; Robert S. Langer, Newton, Mass.

[73] Assignees: Massachusetts Institute of Technology, Cambridge, Mass.; The Penn State Research Foundation, University Park, Pa.

[*] Notice: The term of this patent shall not extend beyond the expiration date of Pat. No. 5,308,701.

[21] Appl. No.: 210,018

[22] Filed: Mar. 18, 1994

Related U.S. Application Data

[60] Continuation of Ser. No. 880,248, May 8, 1992, Pat. No. 5,308,701, which is a division of Ser. No. 593,684, Oct. 5, 1990, Pat. No. 5,149,543.

[51] Int. Cl.⁶ .............................. B01J 13/02; A61K 9/50
[52] U.S. Cl. .................... 424/489; 428/402.22; 424/486; 424/499; 424/497
[58] Field of Search .................................. 424/486, 488, 424/499, 501, 497

[56] References Cited

U.S. PATENT DOCUMENTS

| | | | |
|---|---|---|---|
| 3,773,919 | 11/1973 | Boswell et al. | 424/486 |
| 4,016,078 | 4/1977 | Saeki et al. | 428/402.22 |
| 4,021,364 | 5/1977 | Speiser et al. | 428/102.22 |
| 4,352,883 | 10/1982 | Lim . | |
| 4,440,921 | 4/1984 | Allcock et al. | 528/168 |
| 4,765,973 | 8/1988 | Heller | 424/486 |
| 4,880,622 | 12/1989 | Allcock et al. . | |
| 4,908,233 | 3/1990 | Takizawa et al. | 424/501 |
| 5,089,272 | 2/1992 | Shioya et al. | 424/493 |
| 5,120,349 | 6/1992 | Stewart et al. | 424/408 |
| 5,132,117 | 7/1992 | Speaker et al. | 428/402.21 |
| 5,277,979 | 1/1994 | Lielbanca et al. | 424/462 |
| 5,308,701 | 5/1994 | Cohen et al. | 428/402.22 |

FOREIGN PATENT DOCUMENTS

| | | |
|---|---|---|
| 0127989 | 12/1984 | European Pat. Off. . |
| 60-34731 | 4/1983 | Japan . |
| 2145992 | 4/1985 | United Kingdom . |

OTHER PUBLICATIONS

Sanders et al. J. Pharm. Sci. Journal. Pharm. vol. 73 pp. 1294–1297.

Allcock, et al., *Macromolecules*, vol. 10, No. 4, pp. 824–830 (1977).

*Primary Examiner*—Peter F. Kulkosky
*Attorney, Agent, or Firm*—Arnall Golden & Gregory

[57] ABSTRACT

A method for encapsulating biologically-labile materials such as proteins, liposomes, bacteria and eucaryotic cells within a synthetic polymeric capsule, and the product thereof, are disclosed. The method is based on the use of a water-soluble polymer with charged side chains that are crosslinked with multivalent ions of the opposite charge to form a gel encapsulating biological material, that is optionally further stabilized by interactions with multivalent polyions of the same charge as those used to form the gel. In the preferred embodiment, hydrolytically stable polyphosphazenes are formed of monomers having carboxylic acid side groups that are crosslinked by divalent or trivalent cations such as $Ca^{2+}$ or $Al^{3+}$, then stabilized with a polycation such as poly-L-lysine. A variety of different compositions can be formed from the crosslinked polymer. In a preferred embodiment, microcapsules are made by spraying an aqueous solution of polyphosphazene and material to be encapsulated into a calcium chloride solution.

14 Claims, 3 Drawing Sheets

5,494,682

IONICALLY CROSS-LINKED POLYMERIC MICROCAPSULES

This invention was made with government support under Contract Number NIH-5-R01-AI24764-03 awarded by the National Institutes of Health. The government has certain rights in the invention. This application is a continuation of U.S. Ser. No. 07/880,248, filed on May 8, 1992, now U.S. Pat. No. 5,308,701, which is a divisional of U.S. Ser. No. 07/593,684, filed on Oct. 5, 1990 (now U.S. Pat. No. 5,149,543).

BACKGROUND OF THE INVENTION

This invention relates to a method for preparation of polymer compositions for encapsulation of biological materials, especially living cells.

A number of different polymers have been used for controlled drug delivery. Synthetic polymers are preferred over natural polymers for their reproducibility and ease of manufacture. Examples of biodegradable polymers include poly(anhydrides), poly(orthoesters), and poly(lactic acid). Examples of "non-degradable" polymers include ethylene vinyl acetate and poly(acrylic acid). The use of polyphosphazenes for controlled drug delivery was described in U.S. Ser. No. 07/060,770 filed Jun. 10, 1987, now abandoned, by Laurencin, et al., and in U.S. Pat. No. 4,880,622 to Allcock, et al. The polymers described by U.S. Pat. No. 4,880,622 to Allcock, et al., and in U.S. Ser. No. 07/060,770 by Laurencin, et al., are formed into drug delivery devices by standard techniques, including dissolution and casting of the polymer into a film or disk, dissolution of the polymer and crosslinking by covalent bonding or by irradiation to form a soft gel, or compression of polymer particles into a disk.

Synthetic polymers are used increasingly in medical science due to the chemist's ability to incorporate specific properties such as strength, hydrogel characteristics, permeability or biocompatability, particularly in fields like cell encapsulation and drug delivery where such properties are often prerequisites. However, harsh conditions, e.g., heat or organic solvents, are always used when encapsulating with these polymers, often causing difficulties in encapsulating sensitive entities, e.g., proteins, liposomes, mammalian cells.

Up until now most entrapment methods used for the microencapsulation of mammalian cells have been based on natural polymers such as agarose or alginates. Agarose gel microbeads can be formed by emulsification of an agarose-parafilm oil mixtures or by using teflon molds. In either case, the temperature-mediated gelation of agarose required the use of temperature extremes which are harmful to cells. Alginate, on the other hand, can be ionically cross-linked with divalent cations, in water, and room temperature to form a hydrogel matrix. Due to these mild conditions, alginate has been the most commonly used polymer for hybridoma cell encapsulation. This polymer can be ionically cross-linked in water to form hydrogels as described in U.S. Pat. No. 4,352,883 to Lim. In this process, an aqueous solution containing the biological materials to be encapsulated is suspended in a solution of a water soluble polymer, the suspension is formed into droplets which are configured into discrete microcapsules by contact with multivalent cations, then the surface of the microcapsules are crosslinked to form a semipermeable membrane around the encapsulated materials.

However, natural polymers display variable biocompatability and some properties can be reproduced only with difficulty, due to impurities in the preparation extracts. Synthetic polymers are better to use because of reproducibility and the chemist's ability to tailor their properties according to specific needs. For purposes of greater control over composition and ease of manufacture, it would be preferable to have a method to encapsulate biological materials using synthetic polymers rather than polysaccharides, as described by Lim. It would also be advantageous to be able to make either biodegradable or non-degradable compositions. To date, no one has been able to encapsulate biological materials in synthetic polymers without using elevated temperatures or organic solvents.

It is therefore an object of the present invention to provide a method and compositions for encapsulating biological materials in synthetic polymers without the use of elevated temperatures or organic solvents.

It is a further object of the present invention to provide a method and compositions for encapsulating biological materials in either hydrolytically degradable or non-hydrolytically degradable synthetic polymers.

SUMMARY OF THE INVENTION

A method for encapsulating biologically-labile materials such as proteins, liposomes, bacteria and eucaryotic cells within a synthetic polymeric capsule, and the product thereof, are disclosed. The method is based on the use of a water-soluble polymer with charged side chains that are crosslinked with multivalent ions of the opposite charge to form a hydrogel encapsulating biological material, that is optionally further stabilized by interactions with multivalent polyions of the same charge as those used to form the hydrogel. In the preferred embodiment, hydrolytically stable polyphosphazenes are formed of monomers having carboxylic acid side groups that are crosslinked by divalent or trivalent cations such as $Ca^{2+}$ or $Al^{3+}$, then stabilized with a polycation such as poly-L-lysine Polymers can be synthesized that degrade by hydrolysis by incorporating monomers having imidazole, amino acid ester, or glycerol side groups.

A variety of different compositions can be formed from the crosslinked polymer. In a preferred embodiment, microcapsules are made by spraying an aqueous solution of polyphosphazene and material to be encapsulated into a calcium chloride solution. A semi-permeable membrane is formed on the microspheres by complexation of the surface carboxylate groups with poly(L-lysine). The nature of the polyion, concentration, and reaction conditions can also be used to modify the permeability of the microcapsules. Examples demonstrate encapsulation of normal eucaryotic cells, liposomes, and biologically-sensitive proteins.

DETAILED DESCRIPTION OF THE INVENTION

Figure 1:
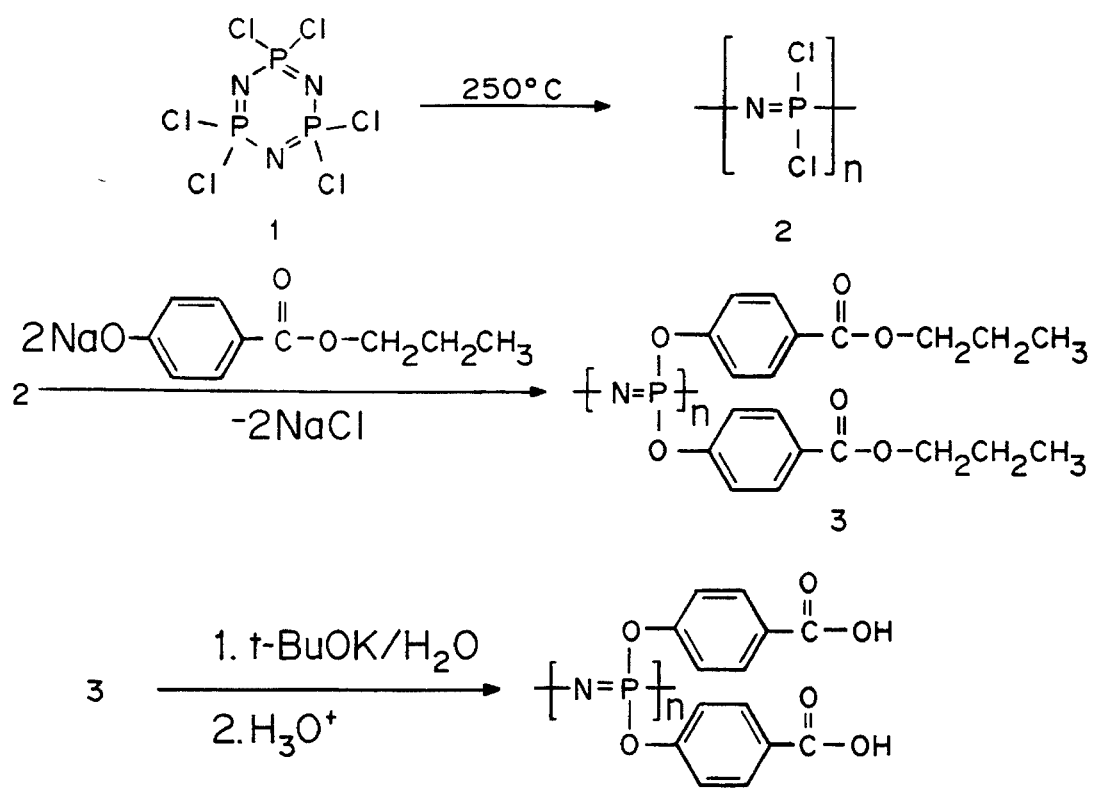
FIG. 1 is a schematic of the synthesis of poly[bis(carboxylatophenoxy)(phosphazene)] (PCPP).

The cross-linked polymer hydrogel is used to encapsulate labile biological materials such as cells, liposomes and proteins. These polymeric compositions can be used as "bioreactors" for cells producing antibodies or recombinant proteins, which can exchange gases and nutrients with the surrounding media while simultaneously protecting the encapsulated materials and retaining the secreted proteins. The compositions can also be used as drug delivery devices and for reinforcement of tissue.

The advantages of the method for making the cross-linkable polymers are that it avoids the use of organic solvents, is highly reproducible and requires few processing steps. The advantages of the synthetic polymers are that they are biocompatible, can be either (or a combination of) hydrolytically degradable or non-degradable, and are soluble in aqueous solutions. The rate of hydrolysis of the polymer can be designed so that it can be processed and remain intact for a desired period of time.

The polymers can be formed into virtually any shape or size, depending upon the physiological environment of use, although microcapsules are preferred for encapsulation of biological material. The polymer can be shaped and sized for buccal, oral, vaginal, intrauterine, ocular, and anal insertion or for parenteral insertion or injection. In the latter instance, the polymers should be in the form of particles small enough to fit through a syringe tip, generally less than a few hundred microns.

In an example of the preferred embodiment of this polymeric material, a polyanionic Poly[bis(carboxylatophenoxy-)phosphazene (PCPP) was synthesized. This was cross-linked with dissolved multivalent cations in aqueous media at room temperature or below to form hydrogel matrices, then a semipermeable membrane formed by interaction with polycations. The entrapment of liposomes and hybridoma cells did not interfere with cross-linking of the polymer with calcium.

This process uses extremely mild conditions for the encapsulation of sensitive entities such as mammalian cells, liposomes and proteins, that had not heretofore been possible with synthetic polymers using known methodology. More than 60% of FITC-BSA and 80% of β-galactosidase were efficiently encapsulated in this system, without loss of enzymatic activity. Hepatocytes and hybridoma cells were also encapsulated and remained viable over extended periods of time. When coated with poly(L-lysine) (PLL; molecular weight 21.5 kD), the gel matrices were able to retain liposomes for more than 50 days. The Ca-PCPP and PCPP-PLL complexes were non-toxic to liver cells and hybridoma cells.

Crosslinkable Water-Soluble Polyelectrolyte Polymers.

There are a number of polymers that can be used to form the cross-linked hydrogel. In general, these are polymers that are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Synthesis and Selection of Polymers.

Polyphosphazenes.

Polyphosphazenes are polymers with backbones consisting of nitrogen and phosphorous separated by alternating single and double bonds. Each phosphorous atom is covalently bonded to two side chains ("R"). The repeat unit in polyphosphazenes has the general structure (1):

(1)

where n is an integer.

The polyphosphazenes suitable for cross-linking have a majority of side chain groups which are acidic and capable of forming salt bridges with di- or trivalent cations. Examples of preferred acidic side groups are carboxylic acid groups and sulfonic acid groups.

In the preferred embodiment, the polyphosphazenes do not hydrolyze in an aqueous environment, so the polymer is not rapidly degraded under in vivo conditions and molecules pass through the polymer substantially by diffusion when the system is exposed to an aqueous environment. In this embodiment, a portion, generally less than 10% of the side chain groups (the R groups in formula 1), are susceptible to hydrolysis.

In a second embodiment, the polymer has at least two differing types of side chains, acidic side groups capable of forming salt bridges with multivalent cations, and side groups that hydrolyze under in vivo conditions, e.g., imidazole groups, amino acid esters, glycerol and glucosyl. The term bioerodible or biodegradable, as used herein, means a polymer that dissolves or degrades within a period that is acceptable in the desired application (usually in vivo therapy), less than about five years and most preferably less than about one year, once exposed to a physiological solution of pH 6–8 having a temperature of between about 25° C.

Hydrolysis of the side chain results in erosion of the polymer. Examples of hydrolyzing side chains are unsubstituted and substituted imidizoles and amino acid esters in which the group is bonded to the phosphorous atom through an amino linkage (polyphosphazene polymers in which both R groups are attached in this manner are known as polyaminophosphazenes). For polyimidazolephosphazenes, some of the "R" groups on the polyphosphazene backbone are imidazole rings, attached to phosphorous in the backbone through a ring nitrogen atom. Other "R" groups can be organic residues that do not participate in hydrolysis, such as methyl phenoxy groups or other groups shown in Allcock, at al., *Macromolecule* 10:824–830 (1977).

The R groups that are not capable of hydrolysis can be any alkyl, aralkyl, or aryl group having 20 carbon atoms or less (more preferably 12 carbon atoms or less); or a heteroalkyl, heteroaralkyl, or heteroaryl group having 20 or less carbons and heteroatoms (more preferably 12 or less carbon or heteroatoms). If the alkyl chain is too long, the polymer will be totally insoluble in water. The groups can be bonded to the phosphorous atom through e.g., an oxygen, sulfur, nitrogen, or carbon atom.

The preferred polyphosphazenes are made by reacting poly(dichlorophosphazene) with the appropriate side chain nucleophiles, which displace the chlorines. Desired proportions of hydrolyzable to nonhydrolyzable side chains in the polymer can be achieved by adjusting the quantity of the corresponding nucleophiles that are reacted with the poly-(dichlorophosphazene). The preferred polyphosphazenes have a molecular weight of over 1,000.

Synthesis of the polymers is described with reference to the following examples employing reagents and equipment as described below. Other equivalent materials can be substituted as necessary. These and other methods for synthesis and the analysis of various types of polyphosphazenes are described by Allcock, H. R.; et al., *Inorg. Chem.* 11, 2584 (1972); Allcock, et al., *Macromolecules* 16, 715 (1983); Allcock, et al., *Macromolecules* 19, 1508 (1986); Allcock, H. R.; Gebura, M.; Kwon, S.; Neenan, T. X. *Biomaterials*, 19, 500 (1988); Allcock, et al., *Macromolecules* 21, 1980 (1988); Allcock, et al., *Inorg. Chem.* 21(2), 515–521 (1982); Allcock, et al., *Macromolecules* 22, 75 (1989); U.S. Pat. Nos. 4,440,921, 4,495,174 and 4,880,622 to Allcock, et al.; U.S. Pat. No. 4,946,938 to Magill, et al., and Grolleman, et al., *J. Controlled Release* 3, 143 (1986), the teachings of which are specifically incorporated herein.

Other water soluble polymers with charged side groups.

Methods for the synthesis of the other polymers described above are known to those skilled in the art. See, for example *Concise Encyclopedia of Polymer Science* and *Polymeric Amines and Ammonium Salts*, E. Goethals, editor (Pergamen Press, Elmsford, N.Y. 1980). Many, such as poly(acrylic acid), are commercially available.

Materials That Can Be Encapsulated.

A number of different materials can be incorporated into the polymeric materials at the time of hydrogel formation, ranging from molecules as small as hormones and proteins such as albumin to macromolecules to living cells such as procaryotic cells and eucaryotic cells, for example, hybridomas, and liposomes.

In the preferred embodiment, materials such as cells, viruses and liposomes are encapsulated within hydrogel microspheres which are subsequently further crosslinked and can be converted into microcapsules by liquification of the core hydrogel. Materials in solution or in suspension can also be encapsulated, including biologically active synthetic compounds, proteins, nucleic acids, polysaccharides, lipids, and other drugs, both synthetic and purified from natural sources.

Examples demonstrate not only encapsulation without loss of activity or viability of cells, but viability of cells over a period of time which can be achieved only if the cross-linked polyphosphazene allows adequate exchange of nutrients and respiratory for the cells to survive.

The ratio of polymer to active agent is determined based on the material that is to be encapsulated, for example, as required to produce a particle size small enough to be injected. Crosslinking of the polymers with multivalent ions to form a hydrogel.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups.

Cross-linking of the Polymers with Acidic Side Groups by Multivalent Cations.

The preferred cations for cross-linking of the polymers with acidic side groups to form a hydrogel are divalent and trivalent cations such as copper, calcium, aluminum, magnesium, strontium, barium, and tin, although di-, tri- or tetra-functional organic cations such as alkylammonium salts, e.g., $R_3N^+$—VVV—$^+NR_3$ can also be used. Aqueous solutions of the salts of these cations are added to the polymers to form soft, highly swollen hydrogels and membranes. The higher the concentration of cation, or the higher the valence, the greater the degree of cross-linking of the polymer. Concentrations from as low as 0.005M have been demonstrated to crosslink the polymer. Higher concentrations are limited by the solubility of the salt.

Cross-linking of the Polymers with Basic Side Groups by Multivalent Anions.

The preferred anions for cross-linking of the polymers to form a hydrogel are divalent and trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

Crosslinking of the Polymers with Multivalent Polyions to Form a Semi-permeable Membrane.

In some embodiments, additional surface groups on the hydrogel polymer are reacted with polyions of opposite charge to form a semi-permeable membrane on the surface of the hydrogel. When the hydrogel is in the form of a microsphere, the core hydrogel can then be liquified by removal of the multivalent ions, for example, by dialysis or addition of a chelating agent. The semi-permeable membrane retains the encapsulated biological material.

Multivalent Polycations Useful for Crosslinking.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. A preferred polycation is poly(L-lysine). Examples of synthetic polyamines are: polyethyleneimine, poly(vinylamine), and poly(allyl amine). There are also natural polycations such as the polysaccharide, chitosan.

The molecular weight of the polycation can affect the thickness of the semi-permeable membrane formed at the surface of the hydrogel. For example, poly(L-lysine) of low molecular weights such as 13–21.5 kDa, can penetrate more easily into the gel matrix to create a membrane with small MW cut-off (i.e., only small proteins with molecular weights less than 68 kDa can diffuse freely through the membrane). However, these membranes are not preferred for culturing of eucaryotic cells, since the openings do not allow adequate exchange of nutrients and respiratory gases to support cell growth and proliferation of cells such as hybridoma cells. Accordingly, for cell encapsulation, poly(L-lysine) of a high molecular weight, MW 102 kDa, is used to complex the hydrogel. These membranes allow cell growth while retaining large molecules such as antibodies.

When a membrane suitable for exchange of the necessary nutrients and respiratory gases is formed around the hydrogel microsphere, and then the hydrogel dissolved around the encapsulated cells, the remaining structure can be used as bioreactors for the production of antibodies or recombinant proteins, as well as in cell transplantation, where the membranes not only retain and support the encapsulated cells, but also prevent the penetration of host immune cells and antibodies.

Multivalent Polyanions Useful for Crosslinking Polymers with Basic Side Groups.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.
Method of Making Microspheres and Microcapsules.

Microsphere Preparation: Gelation with Multivalent Cations.

Microspheres are prepared by spraying an aqueous solution of polymer containing the entity of interest, using a droplet-forming apparatus. The suspension is extruded, for example, from a plastic syringe through a needle located inside a tube through which air flows at a controlled rate. The rate of polymer extrusion is controlled, for example, by a syringe pump. Droplets forming at the needle tip are forced off by the coaxial air stream and collected in the gelation solution (i.e., an aqueous solution of the bi- or trivalent ions), where they cross-link and are hardened, for example, for 15 to 30 minutes.

The shape and size of these microspheres depend on the polymer and cross-linker concentrations and parameters such as the polymer extrusion rate, air flow, and needle diameters used in the microencapsulation procedure.

A typical example for microsphere preparation utilizes PCPP polymer and calcium chloride concentrations of 2.5% and 7.5% (w/v), respectively. With polymer extrusion rate of 70 ml/hour, air flow of 5 L/hour and 20 gauge (G) needle diameter, the resultant microspheres are spherical with diameters in the range of 400–700 micrometers.

Exemplary ranges using PCPP in this method are:
1) final polymer concentrations: 1.25–5% (w/v);
2) calcium chloride concentrations: 3–7.5% (w/v);
3) polymer extrusion rates: 50–100 ml/hour;
4) air flow rates: in the range of 5 L/hour;
5) needle diameters of 18–26 G to produce injectable microspheres. (Macrospheres with millimeter diameters can be prepared by extruding the polymer through pasteur pipets.)

Complexing with Multivalent Polyions.

After hardening in the cross-linker solution, microspheres are collected and further interacted with a charged polyelectrolyte, such as poly(L-lysine) (PLL). The complexed polymer is stable and forms a semipermeable membrane on the microspheres. The permeability of this membrane for a given entity depends on the molecular weight of the polyion.

Preparation of Polymer Microcapsules:

The polyionic-coated hydrogel microspheres are collected and further treated with buffer to remove the uncomplexed multivalent ions, for example, for removal of uncomplexed multivalent cations, 0.9% (w/v) KCl in double distilled water with pH adjusted to pH 8.0. KCl dissolves the internal gel, without affecting the external membrane. Other methods can also be used to liquify the internal gel, including using chelators such as EDTR and sodium citrate.

The methods and compositions described above will be further understood with reference to the following non-limiting examples.

EXAMPLE 1

Synthesis of Polyphosphazenes with Acidic Side Groups.

This synthesis is described by Allcock, et al., *Macromolecules* 22, 75 (January 1989).

The properties of poly(organophosphazenes) can be varied over a wide range by the incorporation of different substituent groups (R). These property changes can be orchestrated with great subtlety both by varying the R group in single-substituent polymers and by the use of two or more cosubstituent groups attached to the same chain. In this way individual polymers may be hydrophobic, amphophilic, or hydrophilic; water-stable or water-erodible; crystalline or amorphous; or bioinert or bioactive.

The synthetic route chosen for the introduction of carboxylic acid containing side groups involves the reaction of the sodium salt of ethyl p-hydroxybenzoate with poly-(dichlorophosphazene), $(NPCl_2)_n$, followed by hydrolysis of the ester function to the carboxylic acid. Preliminary studies were performed with the use of the phosphazene cyclic trimer, $(NPCl_2)_{23}$, as a model for the higher molecular weight polymer.
Experimental Section Equipment. The $^{31}P$ NMR spectra were obtained in the Fourier transform mode with a JEOL FX90Q NMR spectrometer. The $^1H$ NMR spectra were obtained with the same spectrometer operated at 90 MHz. Infrared spectra were recorded by means of a Perkin-Elmer 580 spectrometer. Gel permeation chromatography was carried out with the use of a Hewlett-Packard HP1090 liquid chromatograph with an HP1037A refractive index detector, an HP3329A integrator, and an HP9121 disk drive. The system was controlled by a Hewlett-Packard HP83B computer. A polarizing optical microscope was used to check for crystallinity. Glass transition temperatures ($T_g$) were recorded with the use a Perkin-Elmer DSC 7 instrument with a PE7500 computer.

Materials. Tetrahydrofuran (VWR), dioxane (VWR), and diethyl ether (VWR) were freshly distilled under nitrogen from sodium benzophenone ketyl. Hexachlorocyclotriphosphazene (mp 110°–113° C.) was obtained from a tetramer-trimer mixture (Ethyl Corp.), which was purified by two fractional vacuum sublimations at 60° C./0.5 Torr, two recrystallizations from hexane, and two further vacuum sublimations. Poly(dichlorophosphazene) was prepared by the thermal ring-opening polymerization of hexachlorocyclotriphosphazene at 250° C., described by Allcock, et al., *J. Inorg. Chem.* 5, 1709 (1966). Ethyl p-hydroxybenzoate (Aldrich) was purified by recrystallization from methylene chloride and hexane. Triethylamine (Aldrich) and n-butylamine (Sigma) were purified by vacuum distillation in the presence of calcium hydride, and the distilled amines were stored over molecular sieves before use. Potassium tert-butoxide (Aldrich), p-toluenesulfonic acid (Aldrich), hydrochloric acid (Fisher), dimethyl sulfoxide (Aldrich), calcium chloride (Aldrich), copper chloride (Aldrich), copper bromide (Sigma), and aluminum acetate (Aldrich) were used as received.

Preparation of Compound 4a. Sodium spheres (1.99 g, 0.084 mol) were added to 150 mL of dry dioxane. To the suspension was added ethyl p-hydroxybenzoate (18.7 g, 0.112 mol) dissolved in dry dioxane (30 mL), and the mixture was stirred at reflux for 10 h. To this sodium salt solution was slowly added compound 3a (2.5 g, 7.2 mmol), followed by the addition of tetra-n-butyl-ammonium bromide (0.4 g) to assist complete substitution. The reaction mixture was then stirred at reflux for 72 h. The $^{31}$P NMR spectrum of the solution showed a singlet at +7.7 ppm. The solution was filtered through a 1-in. layer of silica gel, and the solvent was removed by evaporation. The compound was purified by column chromatography with an eluent mixture of methylene chloride and THF (9:1). After drying under vacuum, a bright yellow solid (4a) (82%), mp 78°–80° C., was obtained.

Preparation of Compound 5a. Potassium tert-butoxide (4.43 g, 0.043 mol) was suspended in 100 mL of dry ether. This mixture was cooled to 0° C., and 0.2 mL (0.11 mol) of water was added via syringe. After 5 min of stirring at 0° C., compound 4a (0.5 g, 0144 mmol) was added. The ice bath was removed, and the mixture was allowed to react at room temperature. Thin-layer chromatography tests showed that the starting compound had disappeared completely after 20 h. A large excess of ice water was then added, and the aqueous layer was separated. The isolated aqueous solution was acidified with hydrochloric acid. After three ether extractions, water was removed by evaporation, and the final product was dried overnight under vacuum. A white solid (5a) was obtained (yield 62%). This compound did not melt below 275° C.

Preparation of Compound 6a. Thionyl chloride (10 mL) was added to compound 5a (22 mg, 0.21 mmol). The mixture was heated to reflux and the powder dissolved completely after 1 h. After an additional 1 h, the solution was cooled and the excess thionyl chloride was removed by vacuum drying. The product dissolved in dry THF, was filtered under nitrogen, and was dried overnight under vacuum.

Preparation of Compound 7a. Compound 6a (100 mg, 0.1 mmol) was dissolved in dry THF (20 mL). To the solution was added an excess of n-butylamine (5 mL, 0.068 mol), followed by triethylamine (1 mL) as a hydrochloride acceptor. The mixture was stirred at room temperature for 24 h. The residual amines were removed by evaporation under vacuum to yield 7a, mp 194°–197° C.

Preparation of Polymer 4b. Poly(dichlorophosphazene) (3b) (4 g, 0.0345 mol) was dissolved in dry dioxane (200 mL). The solution was added slowly to the sodium salt of ethyl p-hydroxybenzoate (29.8 g, 0.1794 mol). Tetra-n-butylammonium bromide (0.5 g) was added as a phase-transfer catalyst. The reaction mixture was stirred at reflux for 48 h. A $_{31}$P NMR spectrum contained a singlet at –20.3 ppm. The solution was allowed to cool, and the polymer was isolated by precipitation into water. The polymer was purified by further reprecipitations from THF into water (3 times) and into hexane (twice). The yield was 85%.

Preparation of Polymer 5b. Polymer 4b (0.5 g, 1.33 mmol) was dissolved in dry THF (20 mL). The solution was added slowly to a mixture of potassium tert-butoxide (4 g, 0.04 mol) and 0.2 mL (0.011 mol) of water in dry THF (100 mL). For the first 5 min the mixture was cooled to 0° C.; it was then stirred at room temperature for 40 h. A large excess of ice water (300 mL) was added, and the solution was concentrated by evaporation. The solution was dialyzed through a cellulose tube against deionized water. After dialysis for 72 h, the polymer was isolated by acidification of the solution with hydrochloric acid. The beige-colored polymer was obtained after centrifugation and vacuum drying (yield 85%).

In summary, at the cyclic trimer level, hexachlorocyclotriphosphazene 3a was allowed to react with the sodium salt of ethyl p-hydroxybenzoate to form the ester-type aryloxyphosphazene, 4a. The structure of this compound was confirmed by elemental analysis and by NMR and infrared spectroscopy. For example, the $^{31}$P NMR spectrum showed a singlet at +7.7 ppm, and the H NMR spectrum consisted of two doublets at +7.1 to +8.0 ppm (aromatic protons), a quartet at +4.3 ppm (methylene protons), and a triplet at +1.4 ppm (methyl protons). The infrared spectrum contained a C=O stretch at 1710 cm$^{-1}$ and a P=N/P—O combination band at 1250 cm$^{-1}$.

Hydrolysis of 4a to the carboxylic acid was attempted by several methods, including acidic hydrolysis with hydrochloric acid in tetrahydrofuran or with p-toluene-sulfonic acid or basis hydrolysis with sodium hydroxide. These attempts failed to give the hexacarboxylic acid derivative without decomposition of the skeleton. However, the use of potassium tert-butoxide brought about a clean hydrolysis of 4a to 5a. The structure of 5a was verified by elemental analysis, NMR, and infrared techniques and by derivatization of the carboxylic acid units.

Compound 5a was treated with thionyl chloride to form the acid chloride (6a), and this reacted with n-butylamine in the presence of triethylamine to give the n-butylamido derivative, 7a. The structural proof for this compound was based on the following data. First, the conversion of 4a to 5a and 6a was accompanied by a disappearance of the infrared OH stretching bands but a retention of the skeletal P=N/P—O band at 1250 cm$^{-1}$. The $^{31}$P NMR spectrum of 7a in methylene chloride consisted of a single at +8.45 ppm. The $^1$H NMR spectrum included two doublets at +7.0 to +8.45 ppm (aromatic protons), a quartet at +3.3 ppm (NH—CH$_2$), a multiplet at +1.3 to +1.8 ppm (NHCH$_2$CH$_2$CH$_2$CH$_3$), and a triplet at +0.9 ppm (CH$_3$). The survival of the phosphazene ring throughout these side-group transformations was considered to be favorable evidence that the same reactions might be feasible at the higher molecular weight polymeric level.

Poly(dichlorophosphazene) (3b) was allowed to react with the sodium salt of ethyl p-hydroxybenzoate to form the (aryloxy)phosphazene ester, 4b. Polymer 4b is a microcrystalline, flexible, film-forming material with a glass transition temperature of +7.5° C. and a T$_m$ of 127.4° C. The molecular weight of 4b was estimated by gel permeation chromatography to be in the region of 3×10$^6$. In solid-state properties and in appearance, polymer 4b is similar to poly(diphenoxyphosphazene), [NP(OC$_6$H$_5$)$_2$]$_n$.

Hydrolysis of 4b to the carboxylic acid derivative, 5b, was accomplished with potassium tert-butoxide with the use of reaction conditions similar to those established for the cyclic trimer. Polymer 5b was isolated as a white powder that was insoluble in acidic or neutral aqueous media but soluble in aqueous base. The structures of polymers 4b and 5b were deduced from a combination of microanalysis, $^{31}P$ NMR, and infrared data. For example, after the hydrolysis, the $^{31}P$ NMR spectrum of 5b consisted of a clean single at −19.4 ppm. The $^1H$ NMR spectrum of 5b showed that the quartet at 4.3 ppm and the triplet at 1.4 ppm ($C_2H_5$ groups) had disappeared, but the aromatic protons at 6.8– 7.7 ppm remained. Conversion of the ester (4b) to the carboxylic acid (5b) brought about a slight lowering in the $T_g$ to −4.7° C.

EXAMPLE 2

Cross-linking of Polymer Using Radiation and Covalent Bonding.

In the prior art, polymers were cross-linked chemically or by radiation. The methods and results obtained using polyphosphazenes with acidic side groups were reported by Allcock, et al., in *Macromolecules* (1989), as follows. These methods of crosslinking are not useful in the method of the present invention but are described herein for the purpose of demonstrating the differences between the prior art methods and the method described herein.

Cross-linking by Radiation.

Unlike the water-soluble polymers studied previously in which methylamino (Allcock, et al., *Macromolecules* 21, 1980 (1988)); methoxyethoxyethoxy (Allcock, et al., *Biomaterials* (1990), or protected glyceryl (*Macromolecules* (1988)) side groups were attached to a phosphazene ring, polymer 5b did not cross-link when exposed to gamma radiation. This difference is ascribed to the availability of aliphatic carbon-hydrogen bonds in the first three polymers and their absence in 5b. Attempts to cross-link 5b by chemical condensation of the carboxylic acid groups with di- or trifunctional reagents, such as diamines or glycerol, were impeded by experimental difficulties. The difficulty encountered in the isolation of covalently cross-linked systems after treatment with diamines is due to the limited choice of suitable solvents and the fact that, in solvents such as dimethyl sulfoxide, salt formation precedes covalent coupling. Condensation cross-linking with diols or triols in the presence of dicyclohexylcarbodiimide is difficult to accomplish because of the persistent presence of traces of water in the reactants.

EXAMPLE 3

Ionic Cross-linking of Polymers to Form Hydrogels.

Crosslinking of polyphosphazenes with acidic side groups by di- or trivalent ions was described by Allcock, et al., in *Macromolecules* (1989), the teachings of which are incorporated herein.

Polymer 5b (20 mg, 0.063 mmol) was dissolved in 0.2 mL of sodium carbonate solution (6 mg). To separate polymer solutions were added various concentrations of four different metal salts ($CaCl_2$, $CuCL_2$, $CuBr_2$, and aluminum acetate) in aqueous solutions (0.006–0.09 mmol). The solutions were stirred for 1 min to produce the cross-linked gels. The soluble portion was collected and precipitated by acidification with hydrochloric acid. The uncross-linked polymer was then isolated by centrifugation, washing, and drying under vacuum. The weight of the cross-linked portion was estimated from the weight of the unreacted polymer. The water swellability of the gels was calculated by weighing the fully swelled gel followed by drying under vacuum for 36 h and reweighing the dry gel.

It was found that polymer 5b underwent facile cross-linking in aqueous media when treated with salts of di- or trivalent cations, such as calcium, copper, or aluminum. The amount of water-swelled, cross-linked polymer formed increased as the concentration of calcium chloride, copper chloride, copper sulfate, or aluminum acetate was increased. The markedly greater effectiveness of aluminum ion can be attributed to its trivalent character. In these studies, $Cu^{2+}$ appeared to be a more effective cross-linking agent than $Ca^{2+}$, perhaps because cupric ion has a higher preference for octahedral coordination than does the $Ca^{2+}$ ion or because of the greater Lewis acidity of $Cu^{2+}$ that results from its smaller radius. As a result, the cross-linking process can be understood in terms of "salt bridges" between the chains.

The hydrogels and membranes formed by this process were soft, highly swollen materials. An aluminum ion cross-linked example was found to contain 9.5 g of water for every 1 g of polymer.

The cross-linking process could be effected by immersion of solid films of polymer 5b into aqueous solutions of, for example, copper sulfate. Instead of dissolving, the polymer film swelled as water penetrated the matrix, but the swelling was limited by the diffusion of cupric ions into the polymer. Polymer 5b (100 mg, 0.31 mmol) was dissolved in dimethyl sulfoxide (5 mL). The solvent was removed slowly by evaporation in a dry casting chamber in order to form a uniform and thin film. The dried polymer was then immersed in a solution of copper sulfate (5 g) in 100 mL of water and allowed to swell to the maximum allowed by this cross-linking process. The film was removed from the copper sulfate solution and dried overnight under vacuum.

Ionically cross-linked gels formed by both processes were stable in acidic and neutral media. However, treatment with basic solutions of monovalent cations resulted in cleavage of the ionic cross-links and dissolution of the polymer. This occurred at pH 7.5 for systems cross-linked by $Ca^{2+}$ or $Cu^{2+}$ ions, but the $Al^{3+}$ cross-linked systems required base strengths in excess of pH 9 before the polymer dissolved. Treatment of the $Ca^{2+}$, $Cu^{2+}$, and $Al^{3+}$ cross-linked polymers with excess aqueous potassium chloride at pH 7.5 also resulted in cleavage of the ionic cross-links.

EXAMPLE 4

Formation of Polymeric Hydrogel Microspheres Incorporating Cells or Proteins.

In a preferred embodiment of the method described herein, cation cross-linked polyphosphazene hydrogel microspheres incorporating biological materials were prepared. These were subsequently treated with poly(L-lysine) to form microcapsules having a semi-permeable surface membrane.

As shown in FIG. 1, poly[bis(carboxylatophenoxy)phosphazene] (PCPP) 4 was prepared by first synthesizing poly(dichlorophosphazene) 2 by thermal bulk polymerization of hexachlorocyclotriphosphazene 1. Chlorine atoms were then replaced by carboxylate ester-containing side groups, by reacting propyl p-hydroxybenzoate with 2, forming poly(aryloxy)phosphazene ester 3, followed by hydrolysis of ester groups to carboxylic acids 4. Although the earlier described ethyl ester of the polyphosphazene could also be used, the propyl ester of the polyphosphazene was preferred because it hydrolyzes to the carboxylic acid more readily.

PCPP was insoluble in acidic or neutral solvents but soluble in basis solutions e.g., sodium carbonate. The dissolution of 10% (w/v) PCPP in 30 mg/ml sodium carbonate caused a decrease in solution pH to 7.5–7.8, due to polymer deprotonation, enabling mild encapsulation. When $Ca_{2+}$ was added to PCPP fast gelation occurred.

Microspheres were prepared by spraying aqueous PCPP (2.5% w/v) with FITC-BSA (20 mg; Sigma), or β-gal (1 mg; Sigma #G-5635), or hybridoma cells ($5 \times 10_6$ cells; ATCC HB 123), into 7.5% w/v $CaCl^2$, using a droplet-forming apparatus. The suspension was extruded (at 70 ml/hour) through a 20 G needle located inside a tube through which air flows at 5 L/hour. Droplets forming at the needle tip were forced off by the coaxial air stream and were collected in 7.5% (w/v) $CaCl_2$, where they were cross-linked and hardened for 30 minutes. The shape and size of the resultant microspheres depended on polymer and calcium ion concentrations, polymer extrusion rate, air flow, and needle diameter.

EXAMPLE 5

Cross-linked Polyphosphazene Films Seeded with Hepatocytes.

To examine cellular toxicity, liver cells were isolated from male Fisher rats (Selgen, P. O. In *Methods of Cell Biology*, Prescott, E., ed. p. 13 (Academic Press, N.Y. 1976)) and seeded on Ca-PCPP films coated with PLL. Films were prepared by spreading 1 ml of 2.5% (w/v) PCPP on a 35 mm bacteriological Falcon petri dish, overlaying with 3 ml 10% (w/v) $CaCl_2$, hardening for 15 minutes, draining and coating for 15 minutes with 3 ml 0.25% (w/v) PLL (MW. 21.5 Kd), washing 3 times with buffer (total volume 50 ml) and sterilizing overnight under U.V. light. Films were seeded with $2.5 \times 10_6$ liver cells per dish.

One hour after seeding, cells had attached to the films; washing with media did not remove cells. Microscopic inspection and viability assays (trypan blue dye exclusion and tetrazolium salt assay, Mosmann, T. J., *Immunol. Methods* 65, 55 (1983)) revealed live cells. Five days later, live cells were still observed on films. The results demonstrate that the cross-linked polymer is non-toxic to the cells and supports cell growth and proliferation.

EXAMPLE 6

Cross-linked Polyphosphazene Microspheres Containing Entrapped Proteins.

Ca-PCPP matrices efficiently entrapped fluorescein isothiocyanate-labeled bovine serum albumin (FITC-BSA) and β-galactosidase (β-gal), with MW's of 68 Kd and 540 Kd, respectively; 60% and 80% of FITC-BSA and β-gal, respectively, were recovered in Ca-PCPP spheres. The process enabled high retention of β-gal activity, comparable to its aqueous activity.

Figure 2:
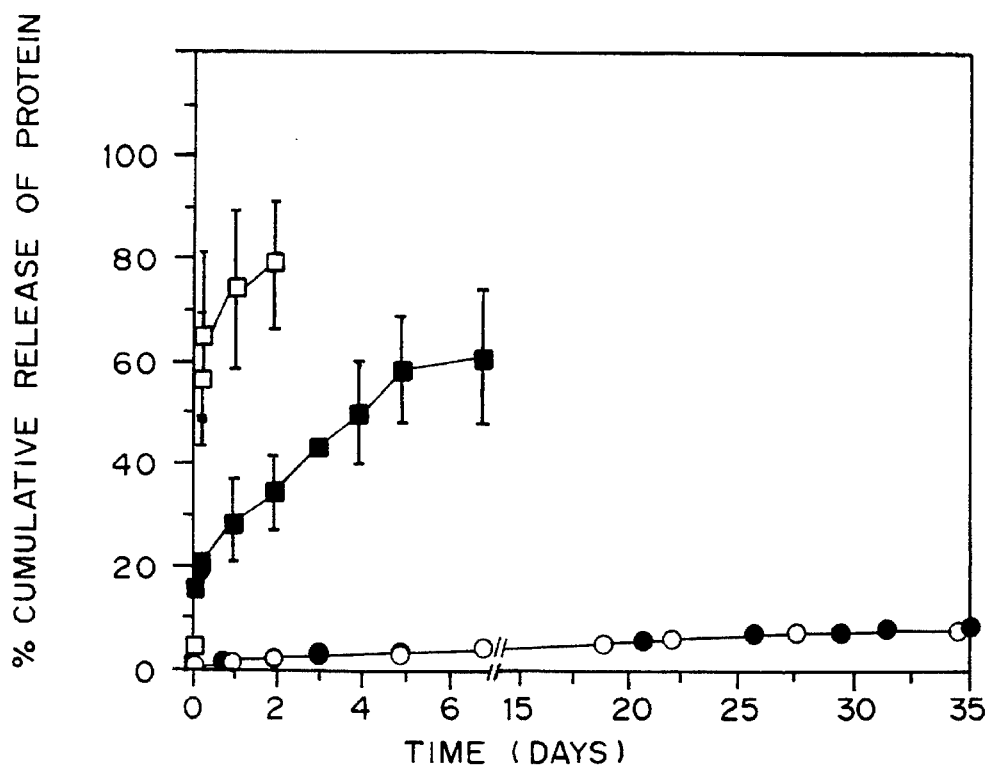
FIG. 2 is a graph of the percent cumulative release rates of FITC-BSA (squares) and β-gal (dark square) from Ca-PCPP spheres coated with 21.5 Kd PLL. FITC-BSA release rates from liposomes (circles) and MELs (dark circles), composed of egg hydrogenated phosphatidylcholine (PPC) and cholesterol (CH), 1:1 molar ratio.

Ca-PCPP spheres aggregate and adhere to glass suggesting surface-charge effects. To neutralize charge (i.e., carboxylic groups), microspheres were reacted with the positively-charged polyelectrolyte, poly(L-lysine)(PLL). Beads were hardened for 30 minutes and coated with 30 ml of 0.25% (w/v) PLL (MW 21.5 Kd; Sigma) for 30 minutes. This not only diminished aggregation, but sustained release rates of FITC-BSA (20%) and β-gal (by 80%), as shown in FIG. 2. Release studies were performed at 37° C., with gentle agitation, in vials containing 10 ml of phosphate-buffered saline (PBS) at pH 7.4, with 0.01% gentamicin sulfate as preservative. FITC-BSA and β-gal release was followed by absorbance at 495 nm and BCA protein assay (Pierce #23235), respectively. The activity of the encapsulated β-gal enzyme is compared with the activity in solution in FIG. 3. The results demonstrate that the enzyme activity is comparable.

EXAMPLE 7

Cross-linked Polyphosphazene Microspheres Containing Liposomes.

FITC-BSA release was further sustained by encapsulating it first in liposomes that were then entrapped in PCPP-PLL, providing microencapsulated liposomes (MELs). Liposomes of hydrogenated phosphatidyl choline (PPC) (Avanti Polar Lips) and cholesterol (CH) (Sigma), 1:1 molar ratio, were prepared by a reverse-phase evaporation, as described by Szoka and Papahadjopoulos; *Proc. Natl. Acad. Sci. USA* 75, 4194 (1978). To prepare MELs, 1 ml of (FITC-BSA)-laden liposomes (66–68 µM lipid) was mixed with 1 ml of 5% (w/v) PCPP and the mixture was sprayed as microdroplets into the $CaCl^2$ solution using the droplet forming apparatus.

Figure 3:
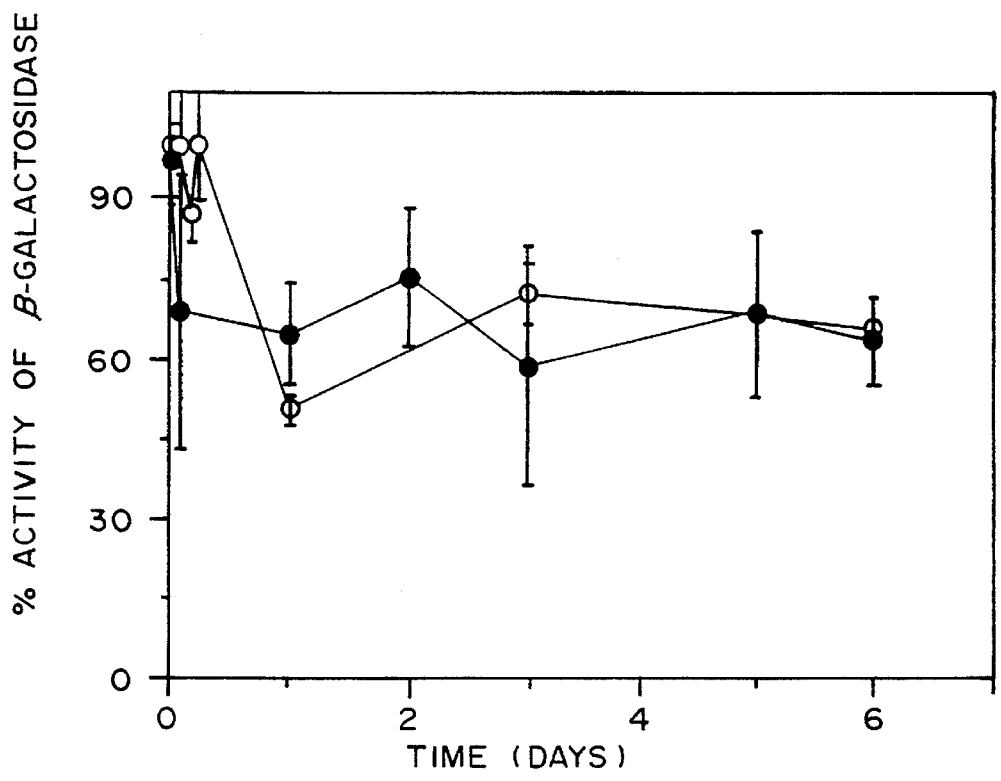
FIG. 3 is a graph of the percent activity of β-galactosidase released from β-gal encapsulated PCPP matrices in phosphate-buffered saline (circle) and β-gal activity in solution (dark circles).

Liposome entrapment did not interfere with ionic cross-linking and, when coated with 21.5 Kd PLL, Ca-PCPP retained them for over 50 days. FITC-BSA release was significantly reduced and was similar to that of unencapsulated liposomes with the same lipid composition, as shown in FIG. 3. The lipid bilayer is presumably rate-limiting for MELs.

EXAMPLE 8

Cross-linked Polyphosphazene Microcapsules Containing Hybridomas.

Cell Lines.

Two lines of mouse hybridoma cells, HFN 7.1 (ATCC CRL) which produce monoclonal antibodies ($IgG_i$) to human fibronectin, and CC9C10 (ATCC HB 123) which secretes monoclonal antibodies ($IgG_ik$) that bind insulin, were used. Continuously growing stock cultures of hybridoma cells were maintained in Dulbecco's Modified Eagle Media (DMEM) 90% (Gibco, N.Y.) supplied with 10% fetal bovine serum (Sigma, Co.,) and 100 units/ml penicillin-streptomycin (Gibco, N.Y.).

Preparation of Polymer Solution.

Poly[bis(carboxylatophenoxy)phosphazene] (PCPP) was synthesized as described above. PCPP was dissolved in sodium carbonate (30 mg/ml) to a final polymer concentration of 10% (W/v). Due to polymer deprotonation the solution pH decreased to 7.5–7.8, and these pH conditions were used during the microencapsulation.

Cell Microencapsulation.

3 ml of culture medium containing approximately $1 \times 10^6$ cells/ml, and viability of 90% (determined by trypan blue exclusion), were pelleted by centrifugation (3000 rpm×5 min). The cell pellets were resuspended in 1 ml sterile phosphate buffered saline (PBS) (Gibco, N.Y.), and mixed with 1 ml of 5% (w/v) PCPP. The cell/PCPP suspension was sprayed as microdroplets using an air jet-head droplet generator equipped with a 22 G needle. The liquid droplets were collected in a sterile solution of 7.5% (w/v) $CaCl_2$, or 5% (w/v) Al $(Ac)_3$, where they were cross-linked by the cations, and gelled. The gel beads were allowed to be hardened for 15 min and then washed with fresh, 5% (w/v) solutions of the cross-linker. The resultant beads were drained, and coated for 20 min by contact with 30 ml of 0.1% (w/v) poly-(L-lysine) (PLL) (Sigma, Co.) in saline, with gentle agitation. Unreacted PLL was removed by washing the beads with 30 ml of PBS. In some cases, after coating with PLL, the interior of the microspheres was liquified by exposure for 30 minutes to 30 ml of sterile isotonic KCl, pH 8. The resultant microcapsules were washed three times with PBS (total volume of 90 ml) to dilute KCl. All the reagents were of analytical grade.

The size and shape of the Ca-PCPP gel beads depended on the initial concentrations of PCPP and $Ca^{2+}$, and factors such as the air flow and needle diameter used in the microencapsulation procedure. At a PCPP concentration of 2.5% (w/v), an air flow of 5 l/min and using a 22 G needle, the capsules were spherical, with diameters in the range of 0.9 mm. The encapsulation of hybridoma cells did not interfere with the formation of a cross-linked hydrogel matrix. However, when polymer gelation was conducted in the presence of culture media, the cross-linking was not complete and resulted in broken capsules. This might be due to interference in polymer cross-linking by the serum proteins. These difficulties were avoided by encapsulating the hybridoma cells in phosphate-buffered saline.

Other studies had shown that Ca-PCPP gel beads disintegrated with time when placed in PBS. This problem did not develop when the cells are coated with poly(L-lysine) and they maintain their characteristic shape. It was also found that when Ca-PCPP microcapsules were incubated with media, supplemented with serum proteins, they maintained their shape and size. Presumably, the continuous presence of metal cations and serum proteins which can interact with the polyanionic polymer helped to maintain the polymer in its crosslinked form.

Cultures were incubated in 8 ml DMEM at 37° C. and 5% of $CO_2$. The cells were fed every two days, by allowing the microcapsules to settle for 2 to 3 minutes, aspirating the spent media, and adding an equal volume of fresh media. Gel bead size determinations were made by examination under a phase contrast microscope equipped with a graticule lens (Nikon TMS).

Cell Number Determinations.

By Trypan Blue:

Aliquots of beads were withdrawn from the cultures and the supernatants were discarded after allowing the gel beads to settle at the bottom of the flask. The beads were incubated for 10 minutes with PBS containing 2 mM ethylenediaminetetraacetic acid (EDTA). This chelator dissolves the interior polymer matrix, making the beads transparent through the external layer of PCPP-PLL. The beads were washed to remove the metal-conjugated EDTA and EDTA, and 100 ml of 0.2% trypan blue dye (Gibco, N.Y.) were added. The number of viable cells were determined by direct counting on a hemacytometer.

By LDH Assay:

Lactate dehydrogenase (LDH) activity was determined using Sigma Kit (LDH/LD No. DG1340-UV). LDH activity can be used to measure cell viability as well as cell number. Cell number was determined by measuring the enzyme activity after cell lysis with detergent (0.2% w/v saponin (Sigma, Co.) in PBS (the lysis buffer). The percent viability was determined by measuring the extracellular LDH without treating the cells with a detergent. A standard calibration curve was constructed using different dilutions of the stock cell culture. The cell samples were lysed by adding a detergent and the activity of the soluble LDH was determined. A linear relationship between the cell number and LDH activity was observed over a cell concentration range of 0 to $8 \times 10^5$ cell/ml.

The number of cells encapsulated in the Ca-PCPP microcapsules was estimated as follows: bead aliquots were collected and washed several times with fresh PBS. The beads were crushed (using a mortar and pestle) in 1 ml of the lysis buffer and incubated for 30 min, at room temperature, to ensure cell lysis. The samples were centrifuged to remove cell and microcapsule debris, and the supernatants were collected. LDH activity was measured at 340 nm using pyruvate as a substrate.

Antibody Quantitations.

The concentration of monoclonal antibody in culture medium was measured by an ELISA against standard antibody solutions. Immulon II plates (Dynatech Labs, Inc.,) were coated overnight with insulin, at 37° C., or human fibronectin, at 4° C. (purchased by Sigma, Co.,), at a protein concentration of 3 mg/well. The wells were further blocked with bovine serum albumin, and washed to remove the excess of unreacted protein. Serial dilutions of culture media were added to the wells, and the plates were incubated for 2 hours, at 37° C., and then rinsed three times with PBS-Tween 20. The assay was resolved using a peroxidase conjugate rabbit antimouse IgG (Organon Teknika). ELISA plates were read on a SLT EAR 400 FW (SLT Lab Instruments, Austria), at 405 against 490 nm.

Intracapsular antibody concentrations were measured as follows: beads cultured with cells were washed several times with PBS, crushed in PBS, and centrifuged to separate the protein product from cell and capsule debris. Serial dilutions of the collected supernatants were analyzed by ELISA as described above. To calculate the antibody concentration in terms of mg per ml of polymer, the bead aliquots were withdrawn, washed with PBS, and dried carefully by absorbing the liquid with a paper tissue. The volume of the polymer was calculated by multiplying the number of beads in the sample by the average volume of one bead (estimated from its radius determined with the microscope).

Trypan blue staining of the cells, and LDH activity studies revealed that more than 25% of the cells were encapsulated inside the Ca-PCPP gels with viability of more than 70%. Photomicrographs of gel-entrapped hybridoma cells immediately, and 10 days after encapsulation in the Ca-PCPP gel beads, show that the cells are dispersed throughout the microcapsule.

The rate of monoclonal antibody production by Ca-PCPP gel-entrapped hybridoma cells was identical to control suspension cultures. Maximal antibody concentrations were detected in the growing media of CaPCPP gel entrapped cells one day after encapsulation. Viability studies showed that 70% of cells were alive. Eighteen days after encapsulation, measurements of the intracapsular antibody concentration reveals that 75% of the released antibody was accumulated inside the bead.

Figure 4:
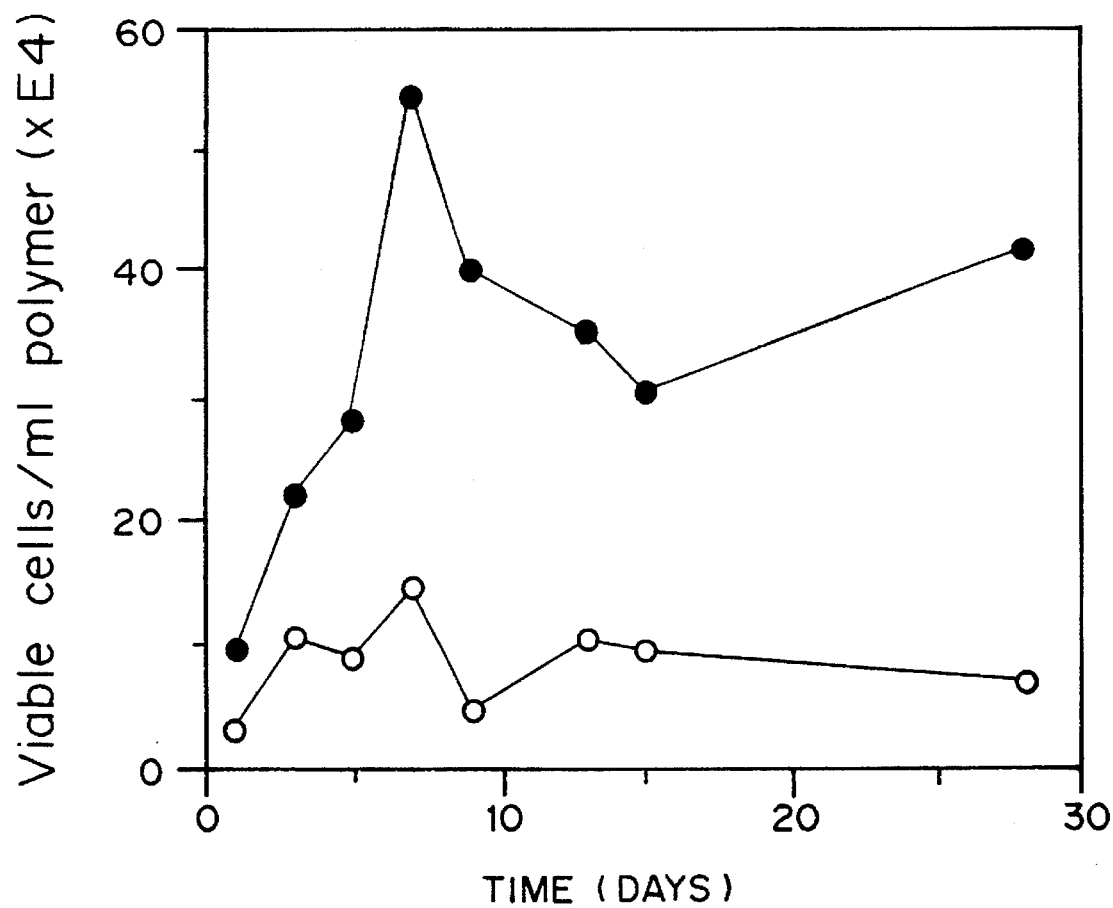
FIG. 4 is a graph of the viable cell/ml polymer over time (days) for cells encapsulated in microcapsules formed by reaction for 15 to 30 minutes with poly(L-lysine) (PLL) with molecular weights between 21.5 and 64 kDa (dark circles) and microcapsules formed by reaction for 20 minutes with PLL with molecular weight of 102 kDa (open circles).

It was found that coating with PLL of MW's in the range of 21.5–64 kDa, and reaction times of 15–30 minutes, produced membranes that inhibited cell growth and proliferation; four days after encapsulation more than 90% of the entrapped cells were dead. Interacting the Ca-PCPP gel beads with PLL of molecular weight 102 kDa, with reaction time of 20 minutes, produced a membrane that enabled cell growth and proliferation. The results, presented in FIG. 4 (open circle), showed a 3 fold increase in cell density after 3 days of encapsulation, within these membranes.

Furthermore, coating with PLL of 102 kDa resulted in the retention of antibody inside the microcapsule. One day after microcapsule preparation, only negligible amounts of antibody were detected in the growing media. By the second day no antibody was detected in culture media. Measurements of intracapsular antibody showed that the protein was accumulated inside the gel microcapsule. Thus, membranes of PCPP and PLL of Mw 102 kDa are efficient for producing concentrated solutions of antibody.

EXAMPLE 9

Effect of Polymer Gelation Conditions on Encapsulation of Cells.

In an effort to increase the percent of cell encapsulation in the methods described in example 7, different polymer gelation solutions were tried: 7.5% (w/v) $CaCl_2$ in double distilled (D.D.) water adjusted to pH 7, 7.5% (w.v) $CaCl_2$ in D.D. water adjusted to pH 4.5, and 5% (w/v) $Al(Ac)_3$, pH 4.5. All other conditions for preparing the microspheres were kept constant.

The highest percent of cell encapsulation, 31%, was achieved with the $Al^{3+}$, pH 4.5 as the polymer gelation conditions; with $Ca^{2+}$, pH 4 5 the value was slightly lower, 25% while when the polymer was gelled with $Ca^{2+}$, pH 7 0, only 10% of the cells were entrapped in the Ca-PP matrix. Lowering the pH (e.g., more protons) enhanced polymer gelation due to protonation of the remaining free, uncrosslinked carboxylic groups.

Cellular productivity (i.e., the amount of monoclonal antibody produced by $10^6$ cells/day), was affected by the gelation conditions of the polymers. The results demonstrate that while polymer gelation with calcium ions did not change cell productivity, the gelation with aluminum ions did; more than 60% of the cell antibody production was lost due to their entrapment in the Al-PP gels. However, cell viability measurements by the LDH assay and trypan blue dye exclusion revealed that the 50% of hybridoma cells were still alive. Presumably, Al ions induced changes in the capability of the cells to produce antibody.

EXAMPLE 10

Effect of Liquefying the Hydrogel Center of Microcapsules Containing Cells.

The effect of liquefying the internal hydrogel on cell growth, proliferation and antibody production, as described in Example 8, was examined by treating the PLL-coated Ca-PCPP beads with 0.9% (w/v) KCl solution, pH 8.0. Under these conditions, the internal gel matrix of Ca-PCPP is dissolved, leaving the outer PCPP-PLL membrane intact. This treatment enabled a fast recovery of the hybridoma cells from the trauma of encapsulation. Moreover, the cell concentration inside the capsule increase by a factor of four. As expected, the increase in cell concentrations inside the PP-PLL capsule led to a concomitant increase in antibody productivity.

In summary, PCPP-PLL matrices provided an efficient membrane bioreactor to increase cell product concentration and thus assist in protein recovery schemes. Another potential use could be as immunoisolation membranes for Islet xenografts when transplanted for treatment of insulin-dependent diabetes mellitus.

Modifications and variations of the method and compositions of the present invention will be obvious to those skilled in the art from the foregoing detailed description.

We claim:

1. A composition in the form of a a microsphere or microcapsule formed by ionically crosslinking a synthetic polymer selected from the group consisting of poly(phosphazenes), poly(acrylic acids), poly(methacrylic acids), copolymers of acrylic acid or methacrylic acid and polyvinyl ethers or poly(vinyl acetate), sulfonated polystyrene, poly(vinyl amines), poly(vinyl pyridine), poly(vinyl imidazole), imino substituted polyphosphazenes, and ammonium or quaternary salts thereof, wherein the polymer is soluble prior to crosslinking in an aqueous solution selected from the group consisting of water, aqueous alcohol, and buffered aqueous salt solutions, with ions selected from the group consisting of calcium, copper, aluminum, magnesium, strontium, barium, organic cations, dicarboxylic acids, sulfate ions and carbonate ions.

2. The composition of claim 1 wherein the polymer has acidic side groups and the ions are cations.

3. The composition of claim 1 wherein the polymer has acidic side chains containing moieties selected from the group consisting of carboxylic acid groups, sulfonic acid groups, halogenated alcohol groups, phenolic OH groups, and acidic OH groups.

4. The crosslinked polymer of claim 1 comprising a hydrolyzable side group.

5. The crosslinked polymer of claim 4 wherein the hydrolyzable side group contains a moiety selected from the group consisting of imidazole, amino acid ester, glycerol, and glucosyl.

6. The composition of claim 1 wherein the polymer has basic side groups and the ions are anions.

7. The composition of claim 1 further comprising a biological material selected from the group consisting of biologically active synthetic compounds, proteins, nucleic acids, polysaccharides, lipids, viruses or virus components, procaryotic cells and components thereof, eucaryotic cells, and liposomes.

8. A method for synthesizing a synthetic polymeric crosslinked composition in the form of a microsphere or microcapsule, the method comprising:

ionically crosslinking droplets of a synthetic polymer selected from the group consisting of poly(phosphazenes), poly(acrylic acids), poly(methacrylic acids), copolymers of acrylic acid or methacrylic acid and polyvinyl ethers or poly(vinyl acetate), sulfonated polystyrene, poly(vinyl amines), poly(vinyl pyridine), poly(vinyl imidazole), imino substituted polyphosphazenes, and ammonium or quaternary salts thereof, and the polymer is soluble prior to crosslinking in an aqueous solution selected from the group consisting of water, aqueous alcohol, and buffered aqueous salt solutions, with ions selected from the group consisting of calcium, copper, aluminum, magnesium, strontium, barium, organic cations, dicarboxylic acids, sulfate ions and carbonate ions.

9. The method of claim 8 wherein the polymer has acidic charged side groups and the ions are cations.

10. The method of claim 8, wherein the polymer has acidic side chains containing moieties selected from the group consisting of carboxylic acid groups, sulfonic acid groups, halogenated alcohol groups, phenolic OH groups, and acidic OH groups.

11. The method of claim 8 wherein the polymer has basic side groups and the ions are anions.

12. The method of claim 8, wherein the polymer further comprises a hydrolyzable side group.

13. The method of claim 12 wherein the hydrolyzable side group contains a moiety selected from the group consisting of imidazole, amino acid ester, glycerol, and glucosyl.

14. The method of claim 8, further comprising encapsulating within the microparticle a biological material selected from the group consisting of biologically active synthetic compounds, proteins, nucleic acids, polysaccharides, lipids, viruses or virus components, procaryotic cells and components thereof, eucaryotic cells, and liposomes.

* * * * *